United States Patent [19]

Driscoll et al.

[11] 4,013,913
[45] Mar. 22, 1977

[54] ION DETECTION ELECTRODE ARRANGEMENT

[75] Inventors: John N. Driscoll, Natick; Frederick F. Spaziani, Lexington, both of Mass.

[73] Assignee: HNU Systems Inc., Newton Upper Falls, Mass.

[22] Filed: Jan. 19, 1976

[21] Appl. No.: 650,531

[52] U.S. Cl. .............................. 313/242; 23/232 E; 250/373; 250/374; 313/240; 313/241
[51] Int. Cl.² .......................................... H01J 1/52
[58] Field of Search .......... 313/239, 240, 241, 242; 250/373, 374; 23/232 E

[56] References Cited
UNITED STATES PATENTS

| 3,591,801 | 7/1971 | Watson et al. | 250/373 |
| 3,918,811 | 11/1975 | Allington | 250/373 |

Primary Examiner—Saxfield Chatmon, Jr.

[57] ABSTRACT

An electrode arrangement for the detection of species ionized by radiant energy from a radiation source, comprising: an annular cathode; a shield, opaque to the radiant energy, extending across the cathode and having an aperture smaller than and coaxial with the annulus formed by the cathode; and an elongated anode having its distal end coaxially of the cathode and the shield aperture, the cathode being shielded from and the anode being exposed to the radiant energy from the radiation source.

21 Claims, 5 Drawing Figures

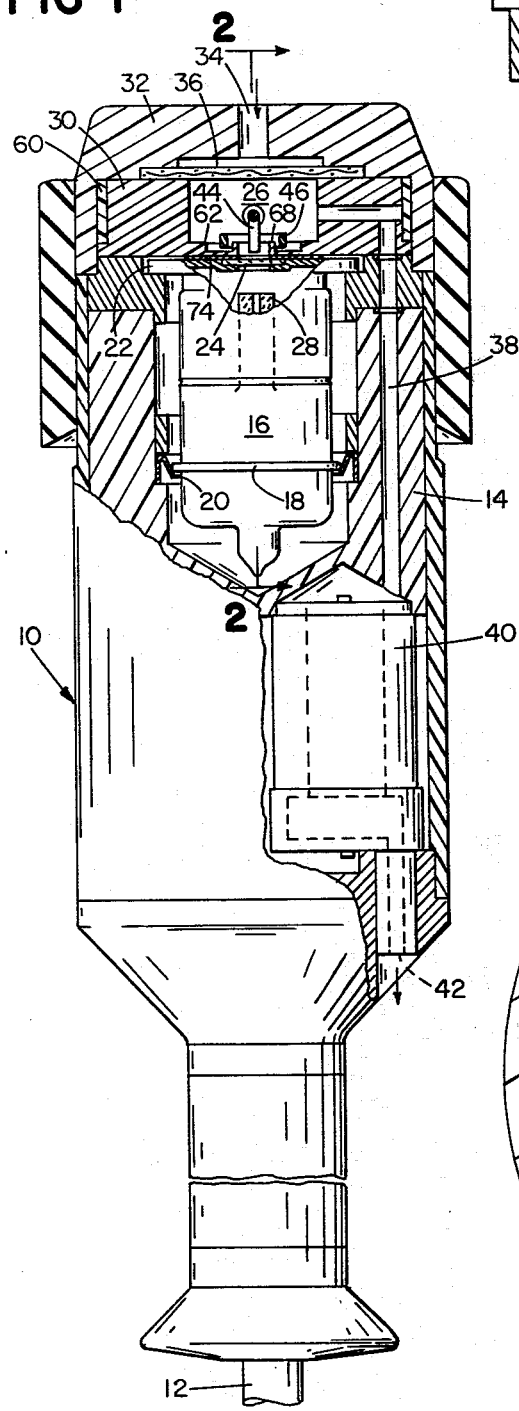

ION DETECTION ELECTRODE ARRANGEMENT

This invention relates to the detection of species ionized by radiant energy and more particularly to an improved ion detection electrode arrangement for use in ionization, especially photoionization apparatus.

It is a principal object of this invention to provide improved sensitivity, extended linearity and reduced effects from background noise in ion detection apparatus.

In general, this invention features, in apparatus including a radiation source for ionizing species, an annular cathode defining an annulus in a plane transverse to the path of energy radiated by the source. An elongated anode is provided with its distal end centrally of the cathode. A radiation shield of material opaque to radiant energy from the source is positioned between the cathode and the source. The shield has an aperture therethrough the edge of which is spaced inwardly of the cathode annulus to prevent impingement of radiant energy on the cathode. Thus, the cathode is shielded from the radiant energy while the anode is directly exposed thereto.

In preferred embodiments, the radiation shield is rigid, electrically non-conductive and chemically inert, such as a fluorinated hydrocarbon organic plastic or a ceramic insulating material. The edge of the aperture in the shield forms an acute angle with the cathode relative to a plane normal to the axis along which energy is radiated from the source.

In preferred embodiments, a metallic electrostatic shield is interposed between the cathode and radiation shield on one side thereof, and the source on the other side thereof. The electrostatic shield has an aperture aligned with the cathode and the radiant energy shield aperture and extends inwardly of the cathode annulus a distance no greater than to the edge of the radiant energy shield aperture. Preferably, an electrically non-conductive material, such as an organic plastic material is positioned between the electrostatic shield and the radiation source.

In preferred embodiments, the cathode, the anode and the shield apertures are coaxial along the energy axis of the source. The cathode is a continuous ring and is supported in a spaced relationship relative to radiant energy shield. The cathode has an inner annular side extending parallel to the energy axis and the radiation shield extends a limited distance parallel to the axis within and spaced from the cathode partially overlying the inner side of the cathode. The anode extends to a position closely adjacent the radiation source and in one embodiment is tubular for conveying samples therethrough to adjacent the energy source, the exit ports therefrom being on the sides thereof and the end thereof being closed.

Other objects, features and advantages of this invention will be apparent to those skilled in the art from the following detailed description of a preferred embodiment thereof, taken together with the accompanying drawings, in which:

FIG. 1 is a side elevation, partly in section, of photoionization apparatus embodying the invention;

FIG. 2 is an enlarged elevation in section of a portion of the apparatus illustrated in FIG. 1, rotated 90° from the position shown in FIG. 1;

FIG. 3 is a view taken along the line 3—3 of FIG. 2;

Figure 4:
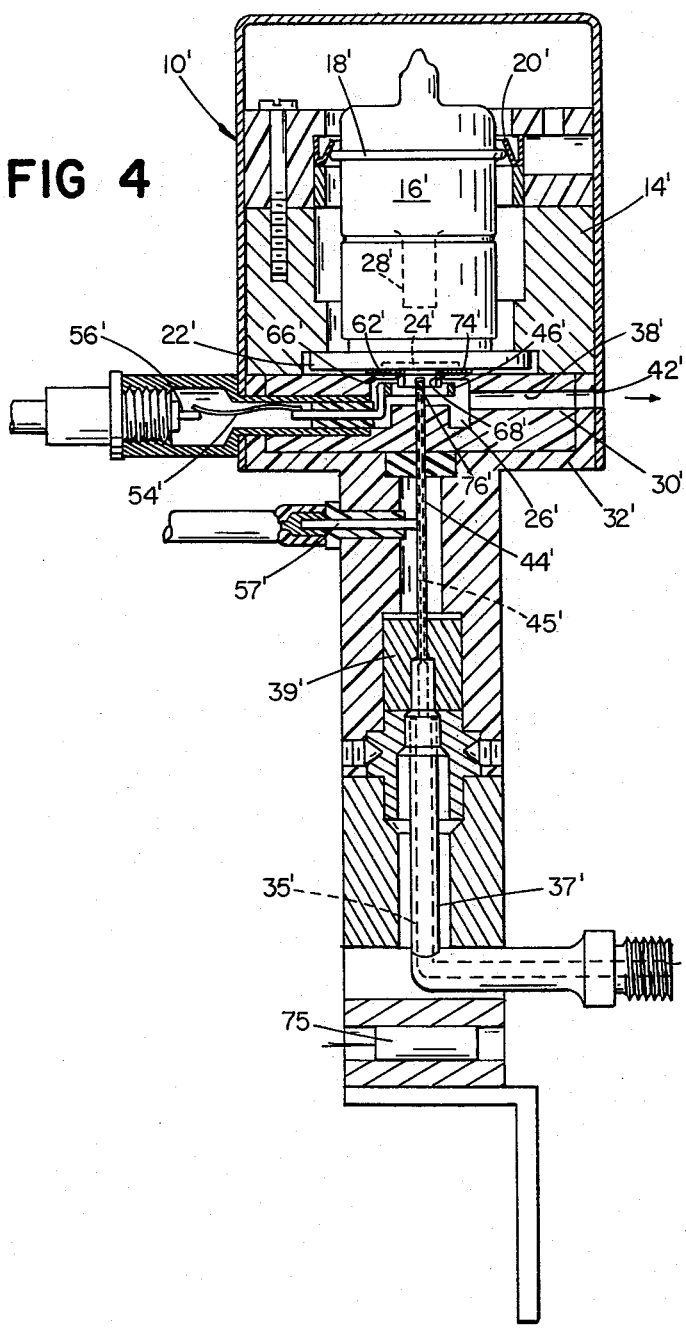
FIG. 4 is a side elevation, in section, of modified photoionization apparatus embodying the invention and adapted for use in chromatographic applications.

In FIG. 1 there is illustrated a hand-held sensor of a trace gas analyzer. The sensor comprises a body 10 having a cable 12 extending therefrom to the analyzer, comprising the instrument power source, controls and readout, forming no part of the present invention and, therefore, not shown.

Within body 10, a recessed housing 14 contains a radiation source 16, i.e. a low pressure Krypton filled lamp for producing monochromatic vacuum ultraviolet radiation (1236 A, having an energy level of 10.oeV). Lamp 16 has its cathode 18 in contact with electrical connector 20 and its anode 22 in contact with another electrical connector (not shown), both connectors connected by suitable cables (not shown) to the power source. Lamp 16 has a circular ultraviolet transmitting window 24 of magnesium fluoride, exposed to a cylindrical photoionization chamber 26 there adjacent. A glass capillary 28 is provided in the lamp 16 to collimate the radiant energy emission therefrom.

Photoionization chamber 26 is formed in an annular recess, coaxial of lamp 16, in electrode support 30. A cover 32 extends across chamber 26 at the end thereof opposite lamp 16. A gas inlet 34 extends through cover 32 to chamber 26, coaxially thereof. A protective screen 36 is mounted between support 30 and cover 32 extending across inlet 34. A gas passage 38 extends through support 30 to a fan 40 in housing 14, the fan 40 arranged to draw gas from inlet 34, through chamber 26 and passage 38, and to exhaust the gas through outlet 42.

As best shown in FIGS. 2 and 3, support 30 houses and supports detection electrodes, anode 44 and cathode 46 in chamber 26. Electrodes 44,46 are of gold plated brass material. The electrodes 44,46 are supported in insulated fittings 48 the exterior metal jackets of which are connected by wires 50 to grounding connections 52. The electrodes 44,46 are connected by wires 54 to terminal jacks 56 adapted for connection to the power source (not shown) which positively biases anode 44 to +180V. As shown in the drawings the connection of the electrodes 44,46 and jacks 56 are made in exterior recesses 58 in support 30; the recesses 58 are closed by an outer annular member 60.

Anode 44 extending inwardly from support 30 is bent in chamber 26 to place its distal end closely adjacent window 24, i.e., spaced 0.020 inches therefrom in the illustrated embodiment, coaxially of the axis along which radiant energy is emitted from lamp 16 i.e., coaxially of capillary 28 and window 24. Anode 44 has a diameter of 0.062 inches.

Cathode 46 comprises a continuous annular ring of rectangular cross-section having an inner diameter of 0.375 inches, a material thickness of 0.032 inches, and a height, parallel to the axis of lamp 16, of 0.093 inches. Cathode 46 is coaxial of anode 44 and the energy axis of lamp 16, lying in a plane transverse, i.e., normal, to the axis and parallel to the plane of window 24.

Support 30 is made of material opaque to radiation from lamp 16, e.g., a fluorinated hydrocarbon sold under the trademark "Kel-F" by Westlake Plastics Company of Lenni, Pa., in the illustrated embodiment.

Adjacent lamp 16, support 30 has a portion 62 extending inwardly between the lamp 16 and cathode 46 to provide a radiation shield preventing exposure of cathode 46 to energy from lamp 16. Shield 62 defines a circular aperture coaxial of the energy axis of lamp 16, having an annular wall 64, parallel to the axis of lamp 16, with a smaller diameter, i.e., 0.250 inches, than the inner diameter of the cathode 46. The wall 64 has a height of 0.080 inches. Facing cathode 46, shield 62 is provided with an annular recess 66 whereby wall 64 defines an upstanding shielding lip 68. The outer diameter of lip 68 is 0.320 inches. Cathode 46 is suspended in recess 66, 0.020 inches above the bottom thereof, and by virtue of their respective diameters cathode 64 is spaced from shielding lip 68 and from the outer wall of recess 66, as well. In an axial direction cathode 46 extends above lip 68 a distance of 0.053 inches.

With the electrodes 44,46 thus arranged, the anode 44 is directly exposed to radiant energy from lamp 16 at its point of maximum intensity. The cathode 46, however, though also positioned close to lamp 16, is shielded from exposure to radiant energy by shield 62 and its shielding lip 68. In the illustrated embodiments, the angle formed between the inner edges 70,72 of cathode 46 and lip 68, axially remote from window 24, relative to the axis of the radiation source is about 50°. The angle thus formed substantially shields the cathode from energy emitted through the window 24. Lip 68 shields cathode 46 from both direct and indirect impingement of energy emitted by lamp 16.

As is also best illustrated in FIGS. 2 and 3, interposed between radiation shield 62 and lamp 16, adhesively affixed to shield 62, is an annular electrostatic shield 74. Electrostatic shield 74, in the illustrated embodiment, comprises aluminized organic plastic material (mylar), with the plastic interposed between the aluminum layer and lamp 16 for insulation purposes. Alternatively, a low flux ferromagnetic material, e.g., mu-metal sold under the trademark "Shieldmu" by Russell Industries, Inc., of Lynbrook, New York, may be employed. Electrostatic shield 74 has an inner diameter equal to that of radiation shield 62 and extends outwardly, under cathode 46, beyond window 24 and preferably to the extent of the diameter of photoionization chamber 26.

FIG. 4 illustrates a modification of the photoionization apparatus described above adapted for use in conjunction with a gas chromatograph and with functionally similar parts correspondingly numbered with a prime designation. The major differences of the modified apparatus are in the anode construction, and the gas inlet. The inlet 34' is in a tube 35' adapted for connection to the outlet from a chromatograph (not shown). Tube 35' extends from inlet 34' and bends to locate its passage 37' therewithin coaxially of lamp 16'. A heater 75 is mounted in the apparatus to control the temperature thereof. Mounted to a fitting 39' on tube 35', coaxially of lamp 16' is anode 44' comprising hypodermic stock having a passage therein 45'. Anode 44' extends to adjacent window 24' of lamp 16' to thus convey minute samples directly to the point of maximum energy radiation. To minimize contamination of window 24' exit ports 76' are provided on the side rather than the end of anode 44'. Gas exhausts from chamber 26' through passage 38' to outlet 42' without the need of a fan. Anode 44' is connected by connector 57' to the power source (not shown) which positively biases anode 44' to +300V. The configuration and spacing of the cathode 46', radiation shield 62', its shielding lip 68', and the electrostatic shield 74' are the same as in the previously described embodiment.

Figure 5:
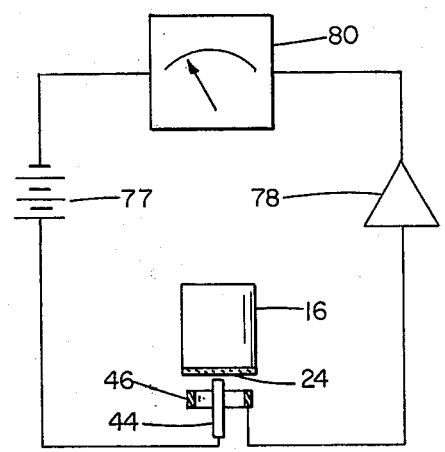
FIG. 5 is a schematic diagram of a detection circuit used with the invention.

FIG. 5 schematically depicts the detection circuit employed with the embodiments shown in FIGS. 1–4. As previously indicated the electrodes in the embodiments are connected to a power source 77 which positively biases the anodes 44(44'). As ionization proceeds in chambers 26(26'), current flow is amplified by amplifier 78 and changes are indicated by a signal processor 80 which may be a meter, as shown, or which may be of the digital type.

Advantageously, the annular cathode configuration with the axial anode permits both anodes to be spaced closely adjacent the radiation source. This has been found to contribute significantly increased sensitivity and linearity compared to parallel plate electrodes. The shielding has been found to significantly reduce the effects of background noise. Shielding lip 68 is particularly useful in minimizing the effects of background noise when low level measurements are being made, e.g., 1–10 ppm. For higher level measurements, however, the range of linearity can be extended significantly by minimizing the height or eliminating lip 68 if the effects of the resultant increase in background noise can be tolerated. The close spacing of the electrodes relative to each other also favorably affects sensitivity and linearity; however, too close spacing may result in an unacceptable increase in noise.

Other embodiments of this invention will occur to those skilled in the art which are within the scope of the following claims.

What is claimed is:

1. An electrode arrangement for detecting ionized species in apparatus comprising a radiation source for ionizing said species and detection electrodes comprising an anode and a cathode, said arrangement comprising:

said cathode having an annular configuration defining an annulus extending in a transverse plane across the axis of radiant energy emission from said radiation source;

said anode having a distal end positioned centrally of said cathode annulus in the path of radiant energy emission from said radiation source; and a shield opaque to said radiant energy extending between said cathode and said radiation source, said shield having an aperture therethrough aligned with said cathode annulus and defining a wall of said shield spaced radially inwardly from said cathode annulus, said anode thereby adapted for direct exposure to said radiant energy through said aperture and said cathode shielded from said radiant energy by said shield.

2. The electrode arrangement claimed in claim 1 in which said shield comprises metallic electrostatic shielding means spaced from said cathode and between said cathode and said radiation source.

3. The electrode arrangement claimed in claim 1 in which said cathode extends axially a predetermined distance and said shield has a lip within said cathode annulus extending axially a distance less than the axial extent of said cathode.

4. The electrode arrangement claimed in claim 3 in which said cathode and said shield are spaced apart from each other.

5. The electrode arrangement claimed in claim 1 in which said shield comprises organic plastic material.

6. The electrode arrangement claimed in claim 1 in which said shield comprises metallic electrostatic shielding material extending outwardly from said aperture beyond said cathode and spaced from said cathode.

7. The electrode arrangement claimed in claim 6 in which said electrodes are positioned in an annular chamber and said electrostatic shielding material extends outwardly to adjacent the edge of said chamber.

8. The electrode arrangement claimed in claim 6 in which said shield also comprises organic plastic material positioned between said cathode and said metallic material.

9. The electrode arrangement claimed in claim 6 in which said electrostatic shielding material comprises a low flux ferromagnetic material.

10. The electrode arrangement claimed in claim 6 in which said metallic material comprises a coating on an organic plastic material and said organic plastic material is positioned between said metallic material and said radiation source.

11. The electrode arrangement claimed in claim 10 in which said shield also comprises organic plastic material positioned between said cathode and said metallic material.

12. The electrode arrangement claimed in claim 11 in which said coating comprises aluminum.

13. The electrode arrangement claimed in claim 1 in which said anode extends along said axis and said distal end is spaced closely adjacent said radiation source, said cathode, and said aperture are coaxial of said axis, and the plane of said cathode is normal to said axis.

14. The electrode arrangement claimed in claim 13 in which said anode is tubular for conveying species to adjacent said radiation source, said anode is closed on its end adjacent said source and has exit ports on the sides thereof adjacent said end.

15. The electrode arrangement claimed in claim 13 in which said cathode is a continuous annulus.

16. The electrode arrangement claimed in claim 15 in which said cathode extends axially a predetermined distance and said shield has a lip within said cathode annulus extending axially a distance less than the axial extent of said cathode.

17. The electrode arrangement claimed in claim 16 in which said cathode and said shield are spaced apart from each other.

18. The electrode arrangement claimed in claim 16 in which said shield comprises fluorinated hydrocarbon plastic material adjacent said cathode and further comprises metallic electrostatic shielding material positioned between said plastic material and said radiation source extending radially inwardly to adjacent said aperture and extending radially outwardly beyond said cathode.

19. The electrode arrangement claimed in claim 18 in which said electrodes are positioned in an annular chamber and said electrostatic shielding material extends outwardly to adjacent the edge of said chamber.

20. The electrode arrangement claimed in claim 18 in which said shield also comprises a second organic plastic material positioned between said metallic material and said radiation source.

21. The electrode arrangement claimed in claim 20 in which said metallic material comprises an aluminum coating on said second plastic material.

* * * * *